US008727617B2

(12) United States Patent
Augais (10) Patent No.: US 8,727,617 B2
(45) Date of Patent: May 20, 2014

(54) DENTAL X-RAY DEVICE AND X-RAY SENSOR

(75) Inventor: Thierry Augais, Les Ulis (FR)

(73) Assignee: Owandy, Croissy Beaubourg (FR)

( * ) Notice: Subject to any disclaimer, the term of this patent is extended or adjusted under 35 U.S.C. 154(b) by 354 days.

(21) Appl. No.: 12/735,777

(22) PCT Filed: Feb. 19, 2009

(86) PCT No.: PCT/FR2009/050265
§ 371 (c)(1),
(2), (4) Date: Aug. 17, 2010

(87) PCT Pub. No.: WO2009/112732
PCT Pub. Date: Sep. 17, 2009

(65) Prior Publication Data
US 2010/0329431 A1 Dec. 30, 2010

(30) Foreign Application Priority Data
Feb. 19, 2008 (FR) ...................................... 08 51045

(51) Int. Cl.
*A61B 6/14* (2006.01)
(52) U.S. Cl.
USPC ............................. 378/170; 378/168; 378/191
(58) Field of Classification Search
USPC ........................ 378/168, 169, 170, 191, 98.8; 250/370.09
See application file for complete search history.

(56) References Cited

U.S. PATENT DOCUMENTS

| 1,667,442 | A | | 4/1928 | Sikes | |
| 5,652,779 | A | * | 7/1997 | Levy et al. | 378/170 |
| 5,691,539 | A | * | 11/1997 | Pfeiffer | 250/370.09 |
| 6,030,119 | A | * | 2/2000 | Tachibana et al. | 378/169 |
| 6,169,781 | B1 | * | 1/2001 | Doebert et al. | 378/98.8 |
| 6,320,934 | B1 | * | 11/2001 | Carroll et al. | 378/98.8 |
| 6,527,442 | B2 | * | 3/2003 | Carroll | 378/189 |
| 6,652,141 | B1 | * | 11/2003 | Cianciosi | 378/191 |
| 6,974,253 | B2 | * | 12/2005 | Ihalainen | 378/191 |
| 7,194,064 | B2 | * | 3/2007 | Razzano et al. | 378/98.8 |
| 7,226,208 | B2 | * | 6/2007 | Schmulenson | 378/168 |
| 7,281,847 | B2 | * | 10/2007 | Kokkaliaris et al. | 378/189 |
| 7,563,026 | B2 | * | 7/2009 | Mandelkern et al. | 378/191 |
| 7,959,355 | B2 | * | 6/2011 | Stantchev | 378/191 |
| 8,320,525 | B2 | * | 11/2012 | Khouri | 378/98.8 |
| 2002/0127512 | A1 | | 9/2002 | Chen et al. | |

FOREIGN PATENT DOCUMENTS

WO    WO 99-44503    9/1999

* cited by examiner

*Primary Examiner* — Allen C. Ho
(74) *Attorney, Agent, or Firm* — Jacobson Holman PLLC (57) ABSTRACT

A dental radiography device has an X-ray sensor (12) with a sensitive surface (22) for detecting X-rays and oriented towards the front face (16) of the sensor and a device for positioning the sensor made up of a receiver (32), for receiving the sensor, and an oblong arm (34) with an end (35) fixed to the receiver and an outwardly directed portion (34B) extending towards the front of the sensor and intended to extend out of the mouth of a patient, the receiver contained in a rear cylindrical space (33B) extending at the rear of a rear face (18) of the sensor opposite the front face (16), the rear cylindrical space (33B) defined by movement, along a lateral edge of the sensor, of a generating straight line (333) perpendicular to the sensitive surface.

12 Claims, 5 Drawing Sheets

DENTAL X-RAY DEVICE AND X-RAY SENSOR

This is a national stage of PCT/FR09/050265 filed Feb. 19, 2009 and published in French, which has a priority of French no. 0851045 filed Feb. 19, 2008, hereby incorporated by reference.

The present invention relates to an intra-oral dental radiography device allowing an intra-oral sensor to be positioned relative to an X-ray beam.

More specifically, the present invention relates to a dental radiography device of the type comprising:

an X-ray sensor which comprises a sensitive surface which is capable of detecting X-rays of an X-ray beam, the sensitive surface being oriented towards a front face of the sensor and a device for positioning the sensor comprising:
  a receiver for receiving the X-ray sensor, the receiver and the received X-ray sensor being intended to be positioned in the mouth of a patient, in particular behind the teeth of the patient to be radiographed, and
  an oblong arm which is intended to extend out of the mouth of the patient, the oblong arm comprising:
    an end fixed to the receiver and
    an outwardly directed portion which extends towards the front of the sensor and which is intended to extend out of the mouth of the patient.

A dental radiography device of this type is sold by the company Unident under the name Universal Holder.

An object of the invention is to improve the quality of the images which are obtained by detecting the X-rays on the sensitive surface and to improve the comfort of the patient.

To that end, the invention relates to a dental radiography device of the above-mentioned type, characterised in that the receiver is contained in a rear cylindrical space which extends at the rear of a rear face of the sensor, opposite the front face, the rear cylindrical space being defined by the movement, along a lateral edge of the sensor, of a generating straight line which is perpendicular relative to the sensitive surface.

By means of the invention, no volume is added laterally to the sensor by the device for positioning the sensor.

According to other features of the invention:
the receiver is configured to allow rotation of the X-ray sensor about an axis of rotation extending within five millimeters or less of a centre of the sensitive surface, preferably at the centre of the sensitive surface;
the device comprises a positioning piece which is fixed to the oblong arm and which is intended to be applied against a cylinder for indicating the position of an X-ray generator which is configured to generate an X-ray beam about a director axis, the positioning piece being such that, when the positioning piece is applied against the cylinder for indicating the position, the director axis of the X-ray beam extends within five millimeters or less of a centre of the sensitive surface, and the sensitive surface is perpendicular to the director axis to within five degrees, preferably the director axis of the X-ray beam is in alignment with the axis of rotation;
the sensitive surface is substantially rectangular and comprises a long side and the X-ray sensor is capable of rotating about the axis of rotation in order to take up a first position, in which the outwardly directed portion is offset from the centre of the sensitive surface in accordance with an axis YY' which is substantially parallel with the long side of the sensitive surface, a second position, in which the outwardly directed portion is offset from the centre of the sensitive surface, obliquely relative to the long side of the sensitive surface, and a third position, which is a mirror image of the second position relative to a straight line which is parallel with the long side and which extends through the centre;
one of the receiver or the X-ray sensor comprises a pin and the other of the receiver or the X-ray sensor comprises a piece for receiving the pin;
the X-ray sensor comprises the pin, the pin projecting backwards, the receiver comprises the piece for receiving the pin;
the X-ray sensor comprises a data transfer cable and the cable extends out of the pin;
the positioning device comprises a system for guiding the cable;
the pin comprises first energy and data exchange means, the receiver comprises second energy and data exchange means, cooperating with the first energy and data exchange means;
the first energy and data exchange means and the second energy and data exchange means are configured to exchange data via rotating electrical contacts;
the first energy and data exchange means and the second energy and data exchange means are configured to exchange data via electromagnetic coupling, preferably via inductive coupling;
the pin is capable of rotating in the receiving piece about the axis of rotation.

The invention also relates to an X-ray sensor for dental radiography of the type comprising a sensitive surface which is capable of detecting X-rays of an X-ray beam, the sensitive surface being orientated towards a front face of the sensor, the X-ray sensor being characterised in that it comprises a pin which is intended to be received in a receiving piece of a device for positioning the sensor, the pin projecting backwards and being located in a rear cylindrical space which extends at the rear of a rear face of the sensor, opposite the front face, the rear cylindrical space being defined by the movement, along a lateral edge of the sensor, of a generating straight line which is perpendicular relative to the sensitive surface.

According to another feature of the invention, the pin is capable of rotating in the circular piece about an axis of rotation and the pin is centred relative to the sensitive surface in such a manner that the axis of rotation extends within five millimeters or less of the centre of the sensitive surface, preferably at the centre of the sensitive surface.

Those features and others of the invention will be appreciated from a reading of the following description of two embodiments of the invention, the description being given with reference to the appended drawings, in which.

Figure 1:
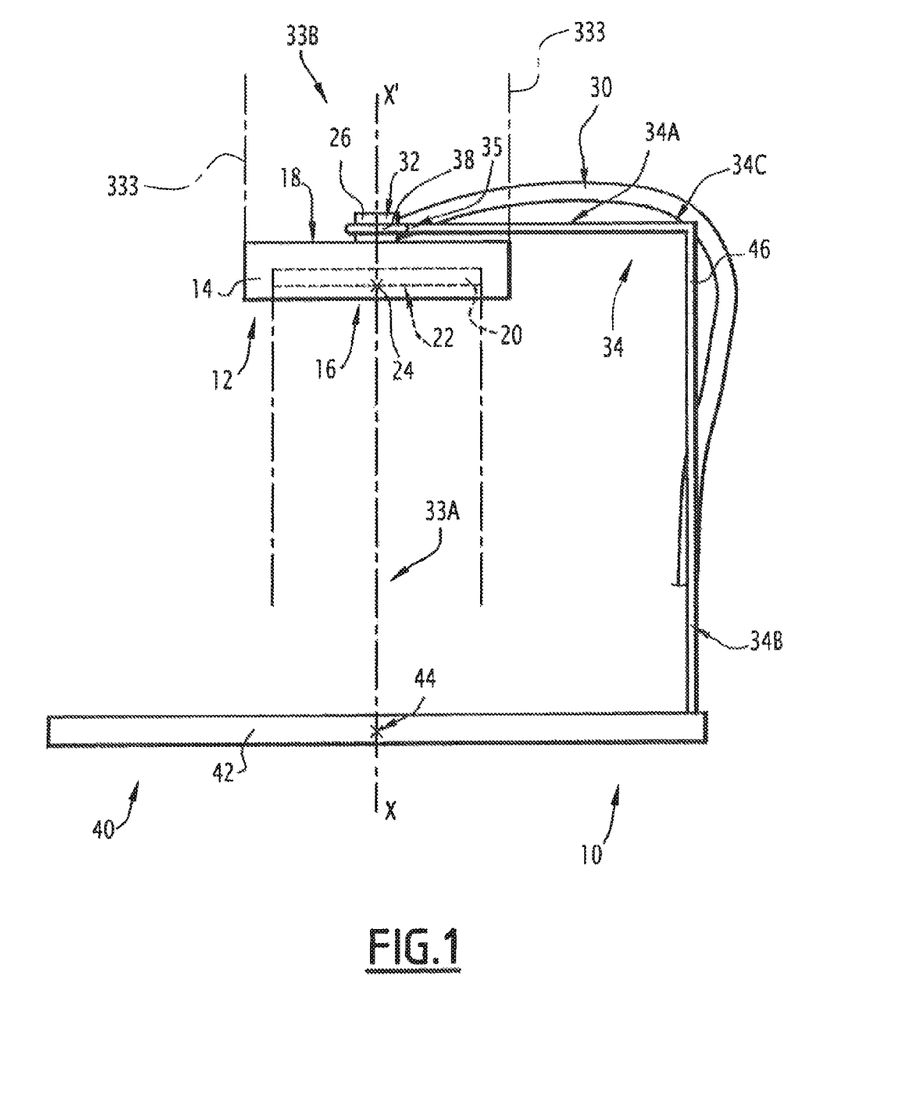
FIG. 1 is a side view of an X-ray sensor and a device for positioning the sensor, according to a first embodiment of the invention.
Figure 2:
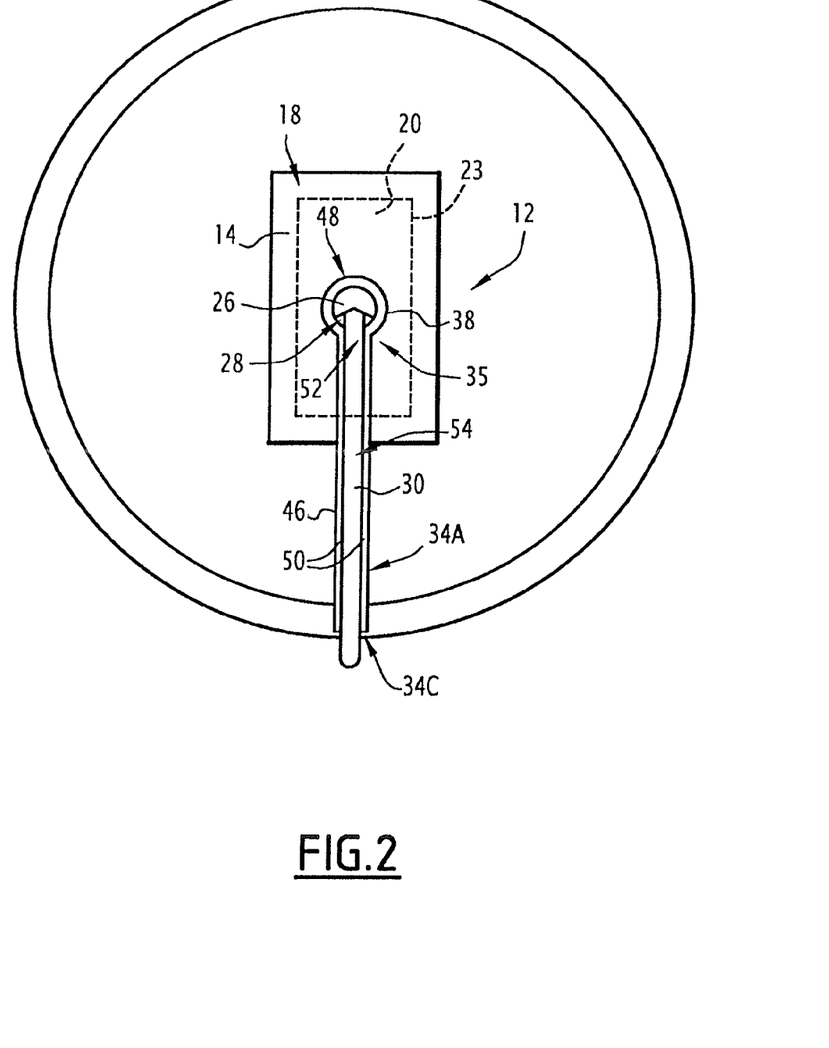
FIG. 2 is a front view of the positioning device and the X-ray sensor of FIG. 1.

FIGS. 1 and 2 illustrate a radiography device according to a first embodiment of the invention, comprising a sensor 12 and a device 10, which is also referred to as an angulator, for positioning the sensor 12.

The sensor 12 comprises a substantially parallelepipedal housing 14 which comprises a large front face 16 and a large rear face 18. The sensor 12 further comprises, in the housing 14, a detector 20 which is capable of detecting X-rays. The detector 20 delimits a surface 22 which is sensitive to X-rays. The sensitive surface 22 is oriented towards the large front face 16. The sensitive surface 22 is delimited by a rectangular periphery 23 and comprises a centre 24 which is, in the example illustrated, the centre of symmetry of the sensitive surface 22. In a variant, the sensitive surface has chamfered corners.

The detector 20 uses CCD technology (charge coupled device) or preferably CMOS technology (photodiode matrix).

The sensor 12 further comprises a substantially cylindrical pin 26. The pin 26 projects, in a backward direction, from the large rear surface 18. The pin 26 is centred about the centre 24 of the sensitive surface 22. An opening 28 is provided in the pin 26. The pin 26 is located in a rear cylindrical space 33B which extends at the rear of the rear face 18 of the sensor 12, opposite the front face 16, the rear cylindrical space 33B being defined by the movement, along a lateral edge of the sensor 12, of a generating straight line which is perpendicular relative to the sensitive surface 22.

The X-ray sensor 12 further comprises a power supply and data transfer cable 30. The cable 30 extends out of the pin 26 via the opening 28, preferably at an angle moving away from the X-ray sensor 12. The opening 28 and, where applicable, the angled outlet allow the cable 30 not to impede the rotation of the X-ray sensor 12 which will be described below.

The sensor 12 is configured, in particular in terms of the materials used, to be introduced into the mouth of a patient.

The positioning device 10 comprises a receiver 32 for receiving the sensor 12 and an oblong arm 34 which is intended to extend out of the mouth of the patient. The receiver 32 is fixed to an end 35 of the arm 34.

The receiver 32 comprises a circular piece 38, in which the pin 26 of the sensor 12 is received. The pin 26 is capable of rotating relative to the circular piece 38 in such a manner that the receiver 32 allows rotation of the sensor 12 about an axis of rotation XX' which is centred about and perpendicular to the sensitive surface 22. The axis of rotation XX' is perpendicular to the sensitive surface to within five degrees and extends within five millimeters or less of the centre 24 of the sensitive surface 22. Preferably, the axis of rotation XX' extends through the centre 24 of the sensitive surface 22. In particular, the opening 28 allows sufficient clearance for the cable 30 so as not to impede rotation.

The receiver 32 is separated from a cylindrical space 33A, which extends towards the front of the sensitive surface 22, defined by the movement, along the periphery 23 of the sensitive surface 22, of a generating straight line which is perpendicular relative to the sensitive surface 22, so as not to screen the sensitive surface 22.

The receiver 32 is further contained in the rear cylindrical space 33B, that is to say, laterally relative to the front/rear direction, within the limits of the X-ray sensor 12. In that manner, the receiver 32 does not increase the lateral spatial requirement of the sensor 12.

The arm 34 comprises a first transverse rod 34A (extending parallel with the sensitive surface 22) which is fixed to the receiver 32 and a second longitudinal rod 34B (extending perpendicularly relative to the sensitive surface 22) which is fixed to the first transverse rod 34A by a bent member 34C.

In that manner, the arm 34 extends from the sensor 12 in such a manner that the first transverse rod 34A comprises the end 35 which is fixed to the receiver 32.

The second rod 34B extends perpendicularly relative to the sensitive surface 22 to within five degrees, and therefore substantially parallel with the axis of rotation XX'. The second rod 34B is shifted/displaced by from 32 to 40 millimeters from the centre 24 of the sensitive surface 22, preferably by 36 millimeters. In that manner, the oblong arm 34 does not obstruct the front cylindrical space 33A.

The positioning device 10 further comprises a positioning piece 40 which comprises a circle 42. The circle 42 is configured to be applied against a cylinder for indicating the position of an X-ray generator, which is configured to generate an X-ray beam about a director axis, in such a manner that the director axis of the X-ray beam is in alignment with the axis of rotation XX'. In that manner, the director axis extends within five millimeters or less of the centre 24 of the sensitive surface 22, and the sensitive surface 22 is perpendicular to the director axis to within five degrees.

The circle 42 comprises a centre 44. The circle 42 is fixed to the second rod 34B in such a manner that the axis of rotation XX' extends within at least two millimeters of the centre 44 of the circle 42, preferably through the centre 44 of the circle 42. That last feature is obtained in that the sum of the radius of the circle 42 and the shift/displacement of the axis of the second rod 34B relative to the edge of the circle 42 corresponds to the displacement of the second rod 34B relative to the centre 24 of the sensitive surface 22, that is to say, is between 32 and 40 millimeters, preferably 36 millimeters.

The circular piece 38 and the oblong arm 34 are constructed by means of a bent metal rod 46 which comprises a rounded portion 48 and two parallel arms 50.

The rounded portion 48 forms the circular piece 38 which is an open ring and consequently comprises an opening 52, through which the cable 30 extends. The two parallel arms 50 together delimit a slot 54. The slot 54 is configured to receive and guide the cable 30 which extends through the opening 52. The opening 52 and the slot 54 thus form a guiding system for the cable 30.

The pin 26 is provided with a circular groove (not illustrated), in which the ring 38 engages during the assembly of the sensor. That assembly is carried out by engaging the angled pin 26 in the ring 38 after positioning the opening 28 perpendicularly relative to the parallel arms 50.

Figure 3:
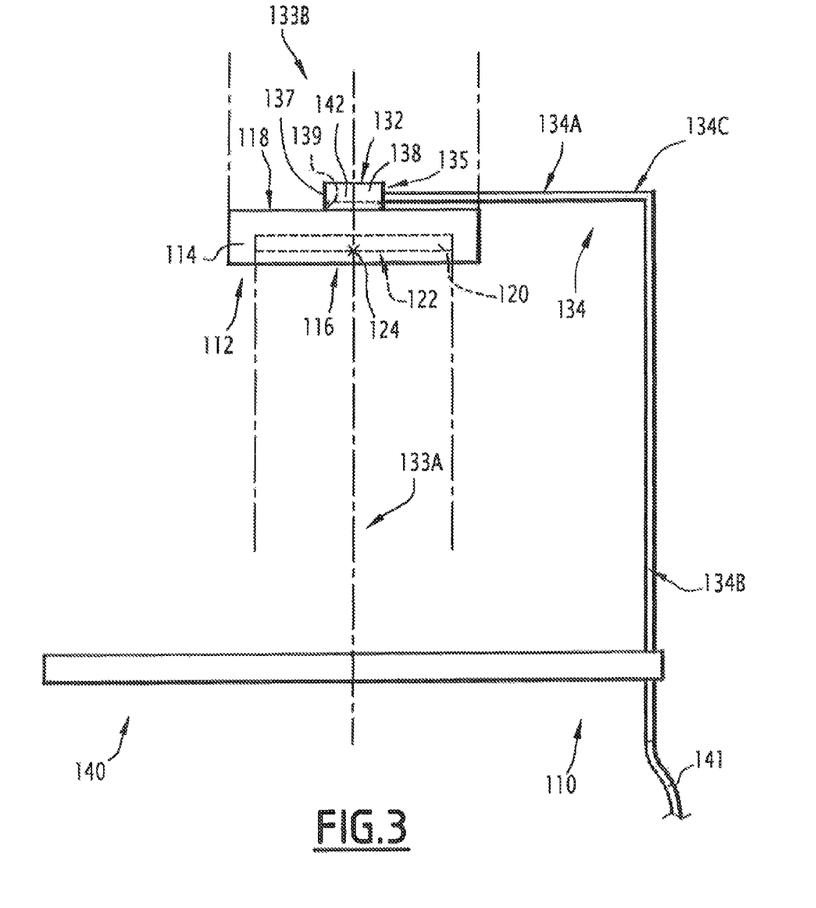
FIG. 3 is a side view of an X-ray sensor and a positioning device according to a second embodiment of the invention.

FIG. 3 illustrates a positioning device 110 and a sensor 112 according to a second embodiment of the invention.

The sensor 112 comprises a substantially parallelepipedal housing 114 which comprises a large front face 116 and a large rear face 118. The sensor 112 further comprises, in the housing 114, a detector 120 which is capable of detecting X-rays. The detector 120 delimits a surface 122 which is sensitive to X-rays. The sensitive surface 122 is orientated towards the large front face 116. The sensitive surface 122 is delimited by a substantially rectangular periphery 123 and comprises a centre of symmetry 124 which is, in the example illustrated, the centre of symmetry of the sensitive surface 122. In a variant, the sensitive surface has chamfered corners.

The detector 120 uses CCD technology (charge coupled device) or, preferably, CMOS technology (photodiode matrix).

Figure 4:
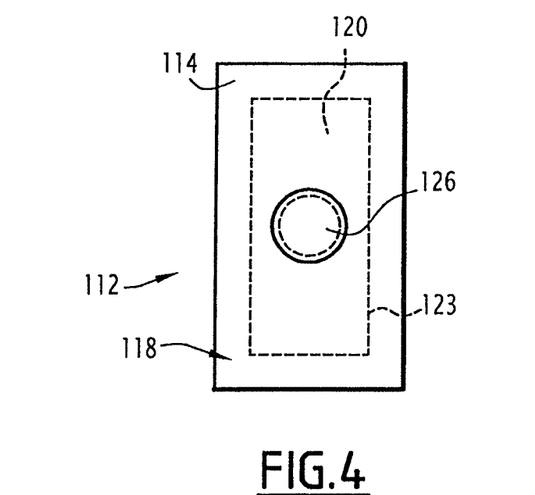
FIG. 4 is a front view of the X-ray sensor of FIG. 3.
Figure 5:
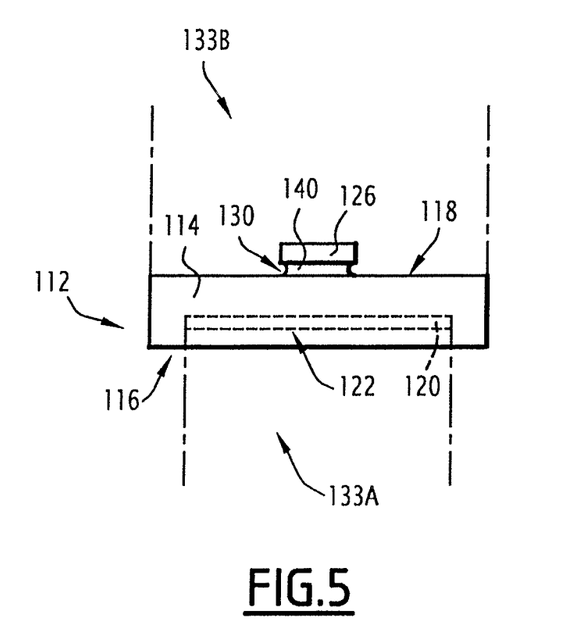
FIG. 5 is a side view of the X-ray sensor of FIG. 3.

With reference to FIGS. 4 and 5, the sensor 112 further comprises a substantially cylindrical pin 126. The pin 126 projects backwards from the large rear surface 118. The pin 126 is centred on the centre 124 of the sensitive face 122. The pin 126 further comprises, over the entire circumference thereof, a groove 130 (visible in FIG. 5). The pin 126 is located in a rear cylindrical space 133B which extends at the rear of the rear face 118 of the sensor 112, opposite the front face 116, the rear cylindrical space 133B being defined by the movement, along a lateral edge of the sensor 112, of a generating straight line perpendicular relative to the sensitive surface 122.

The sensor 112 is configured, in particular in terms of the materials used, to be introduced into the mouth of a patient.

With reference again to FIG. 3, the positioning device 110 comprises a receiver 132 to receive the sensor 112 and an arm 134 which is intended to extend out of the mouth of the patient. The receiver 132 is fixed to one end 135 of the arm 134. The receiver 132 comprises a cap 138 which comprises a side wall 137 forming a circular piece for receiving the pin 126 and delimiting a circular opening, in which the pin 126 of the sensor 112 is received. The circular opening comprises an internal boss 139 (indicated with broken lines in FIG. 3) which is intended to be introduced into the groove 130. The groove 130 and the boss 139 thereby constitute a clip-fit means which allows the pin 126 to be retained in the circular opening of the cap 138, whilst allowing the pin 126 to rotate in the circular opening. The arm 134 can further be readily withdrawn from the sensor, which allows it to be replaced if it is defective, or allows it to be used with another sensor of a different size, that is to say, comprising, for example, a sensitive surface having a different surface-area.

The receiver 132 is contained in the rear cylindrical space 133B, that is to say, laterally relative to the front/rear direction, within the limits of the X-ray sensor 112. In this manner, the receiver 132 does not increase the lateral spatial requirement of the sensor 112.

The pin 126 is circular and is capable of rotating relative to the circular opening in such a manner that the receiver 132 allows rotation of the sensor 112 about an axis of rotation XX' which is centred about and perpendicular to the sensitive surface 122. The axis of rotation XX' is perpendicular, to within five degrees, and extends within five millimeters or less of the centre 124 of the sensitive surface 122. Preferably, the axis of rotation XX' extends through the centre 124 of the sensitive surface 122.

The arm 134 comprises a first transverse rod 134A (extending parallel with the sensitive surface 122) which is fixed to the receiver 132 and a second longitudinal rod 134B (extending perpendicularly to the sensitive surface 122) which is fixed to the first rod 134A by a bent member 134C. In that manner, the arm 134 extends round the sensor 112 in such a manner that the end 135 is fixed to the receiver 132 in the rear cylindrical space 133B.

The second rod 134B extends perpendicularly to the sensitive surface 122 to within five degrees, and therefore substantially parallel with the axis of rotation XX'. The second rod 134B is shifted/displaced by from 32 to 40 millimeters from the centre 124 of the sensitive portion 122, preferably by 36 millimeters. In that manner, the oblong arm, 134 does not obstruct the front cylindrical space 133A which extends towards the front of the sensitive surface 122, defined by the movement, along the periphery 123 of the sensitive surface 122, of a generating straight line which is perpendicular to the sensitive surface 122.

The angulator 110 further comprises a positioning piece 140 which is identical to the positioning piece 40 of the first embodiment.

In order to replace the connection cable conventionally used in intra-oral sensors, the pin 126 comprises first energy and data exchange means 140 whilst the receiver 132 comprises second energy and data exchange means 142 which cooperate with the means 140. The energy exchanged by the means 140 and 142 allow the X-ray sensor 112 to be supplied with electrical power.

The arm 134 is configured to transfer the data, for example, by integrating a cable or electrical conductors as far as a connection cable 141, or as far as a connector (not illustrated) which is intended to connect the connection cable. The connection cable connects the radiography device to an electronic housing for processing the data provided by the X-ray sensor 112.

In a first embodiment, the first energy and data exchange means 140 and the second energy and data exchange means 142 are configured to exchange data via rotating electrical contacts.

In a variant, the first energy and data exchange means 140 and the second energy and data exchange means 142 are configured to exchange data via electromagnetic coupling, of the inductive or capacitive type, or via optical means. Those means can also be used in a mixed manner. The coupling is preferably inductive.

It is possible to refer to the products P-cores P11/7/I of the company Ferroxcube to find an example of a magnetic circuit which is capable of bringing about the energy and data exchange via inductive coupling, provided that two of those magnetic circuits of the windings are provided with adequate turns.

There will now be explained the operation of the X-ray sensor and the positioning device, both for the first and the second embodiments of the invention.

Since the sensitive surface 22, 122 is substantially rectangular, it has two long opposing sides 150, 152 and two short opposing sides 154, 156.

A first type of dental radiography is a radiography referred to as a horizontal bite-wing. It involves simultaneously radiographing the upper portion and the lower portion of the teeth. In that case, with reference to FIG. 6, the sensor 12, 112 is rotated into a first angular position, in which the second rod 34B, 134B is shifted/displaced from the centre 24, 124 of the sensitive surface 22, 122 in accordance with an axis YY' (corresponding to the first transverse rod 34A, 134A) which is substantially parallel with the long side 150 of the sensitive surface 22, 122. That position allows the teeth to the left or right to be radiographed by pivoting the assembly constituted by the sensor and the positioning device simultaneously through 180°.

Figure 6:
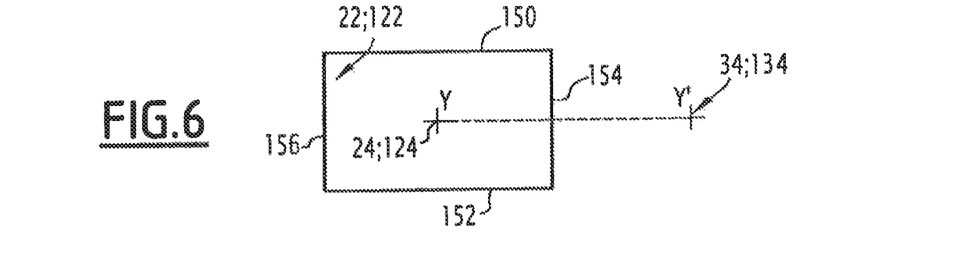
FIGS. 6 to 8 are diagrams illustrating the relative positions of a rod of the positioning device and a sensitive surface of the sensor.

With the sensor being rotated through 90° relative to the preceding position (the axis YY' is substantially parallel with the short sides 154, 156), a second position is obtained allowing a vertical bite-wing to be carried out.

Figure 7:
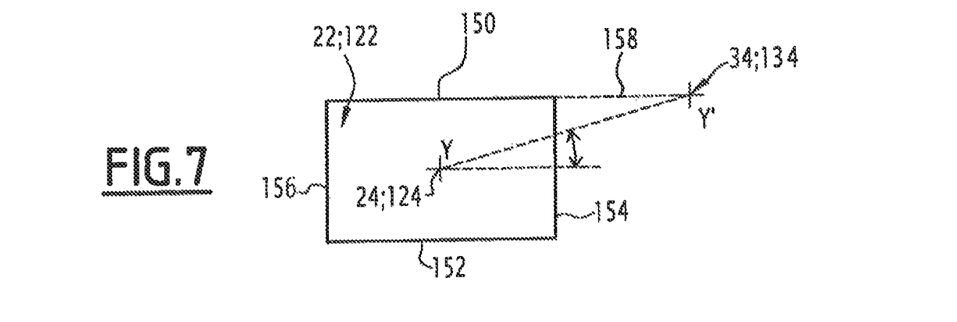

A second type of radiography is called "posterior". It involves radiographing the bottom of the upper or lower teeth, to the right or left, that is to say, four zones to be radiographed. In that type of radiography, the sensor 12, 112 extends along the teeth, that is to say that the long sides 150, 152 are parallel with the occlusal plane. In that case, with reference to FIG. 7, the sensor 12, 112 is rotated into a third angular position, in which the arm 34, 134 is rotated about the center 24, 124 of the sensitive surface 22, 122 in accordance with an axis YY' (corresponding to the first transverse rod 34A, 134A) so that the second rod 34B, 134B is substantially on the straight line 158 extending the long side 150. In that angular position, it is possible to reach two opposing zones to be radiographed, for example, the upper right-hand teeth and the lower left-hand teeth. The other two zones will be reached by rotating the sensor 12, 112 into a fourth angular position (not illustrated) which is symmetrical relative to the third angular position relative to a straight line which is parallel with the long side 150 and which extends through the center 24, 124 in such a manner that the second rod 34B, 134B is offset from the center 24, 124 of the sensitive surface 22, 122 in accordance with an axis YY' so that the second rod 34B, 134B is substantially on the straight line which extends the long side 152.

Figure 8:
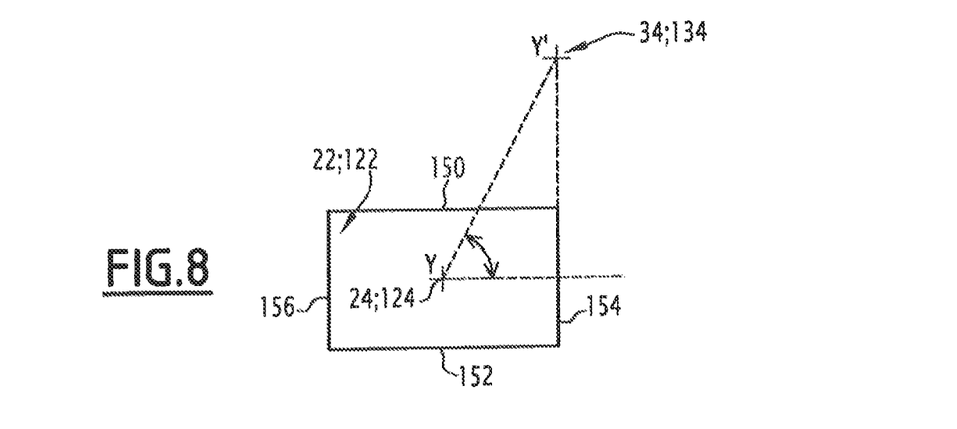

A third type of dental radiography is called "periapical". That type of radiography is identical to the "posterior" type of radiography, except that the sensor 12, 112 must be rotated perpendicularly relative to the occlusal plane. In that instance, with reference to FIG. 8, the sensor 12, 112 is rotated into a fifth angular position, in which the second rod 34B, 134B is substantially in alignment with the short side 154 in order to radiograph two opposing zones of the teeth. In order to radiograph the other two opposing zones of the teeth, the sensor 12, 112 is rotated into a sixth angular position which is symmetrical relative to the fourth angular position relative to a straight line (not illustrated) which is parallel with the long side 150 and which extends through the centre 24, 124.

Preferably, the sensor 12, 112 and/or the support 32, 132 comprises means (not illustrated) for maintaining the sensor 12, 112 in at least some of the six positions, preferably the six positions. Those means are, for example, bosses which are positioned on the sensor 12, 112 and which are intended to cooperate with the receiver 32, 132. Instead, there may be more simply provided visual references which are pad-printed or screen-printed on the sensor and the receiver.

Correspondingly, a check-bite may be fixed to the arm 34, 134. The teeth to be radiographed are intended to press against the check-bite, the check-bite being located so that the sensitive surface 22, 122 begins at the tip of the teeth to be radiographed.

In that manner, the invention allows, with a single positioning device, all types of examination with sensors of different sizes which are developed in order to be used with the positioning device to which the invention relates.

The invention also allows an improvement in the comfort of the patient, particularly by minimising all the volumes located in the mouth and particularly those located on the panels of the sensor resulting in constraints on the sensitive tissues of the patient, such as the gums, because the sensor is not surrounded, at its periphery, by any piece.

The invention further facilitates disinfection, reliability and maintainability.

The invention claimed is:

1. A dental radiography device comprising:
    an X-ray sensor (12; 112) which comprises a sensitive surface (22; 122) which is capable of detecting X-rays of an X-ray beam, the sensitive surface (22; 122) being oriented towards a front face (16; 116) of the sensor (12; 112); and
    a device for positioning the X-ray sensor comprising:
        a receiver (32; 132) for receiving the X-ray sensor (12; 112), the receiver (32; 132) and the received X-ray sensor (12; 112) being intended to be positioned in the mouth of a patient, behind the teeth of the patient to be radiographed, and
        an oblong arm (34; 134) which is intended to extend out of the mouth of the patient, the oblong arm (34; 134) comprising:
            an end (35; 135) fixed to the receiver (32; 132), and
            an outwardly directed portion (34B; 134B) which extends forward of the sensor (12; 112) and which is intended to extend out of the mouth of the patient,
    the dental radiography device being characterised in that the receiver (32; 132) is contained in a rear cylindrical space (33B; 133B) which extends at the rear of a rear face (18; 118) of the X-ray sensor (12; 112), opposite the front face (16; 116), the rear cylindrical space (33B; 133B) being defined by a movement, along a lateral edge of the sensor (12; 112), of a generating straight line (333) which is perpendicular relative to the sensitive surface (22; 122), one of the receiver (32; 132) or the X-ray sensor (12; 112) comprises a pin (26; 126), the other of the receiver (32; 132) or the X-ray sensor (12; 112) comprises a piece (38; 137) for receiving the pin (26; 126), the pin (126) comprises first energy and data exchange means (140), and the receiver (138) comprises second energy and data exchange means (142), cooperating with the first energy and data exchange means (140).

2. The dental radiography device according to claim 1, further characterised in that the receiver (32; 132) is configured to allow rotation of the X-ray sensor (12; 112) about an axis of rotation (XX') extending within five millimeters or less of a centre (24; 124) of the sensitive surface (22; 122).

3. The dental radiography device according to claim 2, further characterised in that:
    the sensitive surface (22) is substantially rectangular and comprises a long side (150), and the X-ray sensor is capable of rotating about the axis of rotation (XX') in order to take up:
        a first position, in which the outwardly directed portion is offset from the centre (24; 124) of the sensitive surface (22; 122) in accordance with an axis YY' which is substantially parallel with the long side (150) of the sensitive surface (22; 122),
        a second position, in which the outwardly directed portion is offset from the centre (24; 124) of the sensitive surface (22; 122), obliquely relative to the long side (150) of the sensitive surface (22; 122), and
        a third position, which is a mirror image of the second position relative to a straight line which is parallel with the long side (150) and which extends through the centre (24; 124).

4. The dental radiography device according to claim 2, further characterised in that
    one of the receiver (32; 132) or the X-ray sensor (12; 112) comprises a pin (26; 126) and
    the other of the receiver (32; 132) or the X-ray sensor (12; 112) comprises a piece (38; 137) for receiving the pin (26; 126) and
    the pin (26; 126) is capable of rotating in the receiving piece (38; 137) about the axis of rotation (XX').

5. The dental radiography device according to claim 1, further characterised in that the receiver (32; 132) is configured to allow rotation of the X-ray sensor (12; 112) about an axis of rotation (XX') extending at a centre of the sensitive surface (22; 122).

6. The dental radiography device according to claim 1, further characterised in that it comprises a positioning piece (40; 140) which is fixed to the oblong arm (34; 134) and which is intended to be applied against a cylinder for indicating the position of an X-ray generator which is configured to generate an X-ray beam about a director axis, the positioning piece (40; 140) being such that, when the positioning piece (40; 140) is applied against the cylinder for indicating the position:
    the director axis of the X-ray beam extends within five millimeters or less of a centre (24; 124) of the sensitive surface (22; 122), and
    the sensitive surface (22; 122) is perpendicular to the director axis to within five degrees, preferably the director axis of the X-ray beam is in alignment with the axis of rotation (XX').

7. The dental radiography device according to claim 1, further characterised in that:
    the X-ray sensor (12; 112) comprises the pin (26; 126), the pin (26; 126) projecting backwards, the receiver (32; 132) comprises the piece (38; 137) for receiving the pin (26; 126).

8. The dental radiography device according to claim 7, further characterised in that the X-ray sensor (12) comprises a data transfer cable (30) and in that the cable (30) extends out of the pin (26).

9. The dental radiography device according to claim 8, further characterised in that the device for positioning the X-ray sensor further comprises a system (52, 54) for guiding the cable (30).

10. The dental radiography device according to claim 1, further characterised in that the first energy and data exchange means (140) and the second energy and data exchange means (142) are configured to exchange data via rotating electrical contacts.

11. The dental radiography device according to claim 1, further characterised in that the first energy and data exchange means (140) and the second energy and data exchange means (142) are configured to exchange data via electromagnetic coupling.

12. The dental radiography device according to claim 1, further characterised in that the first energy and data exchange means (140) and the second energy and data exchange means (142) are configured to exchange data via electromagnetic inductive coupling.

* * * * *